United States Patent [19]
Cohen et al.

[11] Patent Number: 5,827,838
[45] Date of Patent: Oct. 27, 1998

[54] METHOD FOR THE TREATMENT OF DISEASES RELATED WITH PROTEIN ISOPRENYLATION

[75] Inventors: Louis Hartog Cohen, Breukelen; Jacobus Hubertus Van Boom, Voorschoten; Gijsbert Arie Van Der Marel; Adrianus Petrus Robertus Marie Valentijn, both of Leiden, all of Netherlands

[73] Assignee: Nederlandse Organisatie Voor Toegepast-Natuurwetenschappelijk Onderzoek Tno & Rijksuniversteit Te Leiden, Netherlands

[21] Appl. No.: 348,568

[22] Filed: Dec. 2, 1994

Related U.S. Application Data

[63] Continuation-in-part of Ser. No. 957,614, Oct. 6, 1992, abandoned.

[51] Int. Cl.$^6$ .................................................. A61K 31/66
[52] U.S. Cl. ........................ 514/106; 514/102; 514/103
[58] Field of Search ..................... 514/106, 103, 514/102

[56] References Cited

PUBLICATIONS

Kolodyazhay: et al, Dopov. Akad. Nauk Ukr, RSR, Ser B: GEOL, KHIM, Biol. Nauki (1987), (7), 51–3.

The original reference will be presented in due course.

*Primary Examiner*—Jerome D. Goldberg
*Attorney, Agent, or Firm*—Bachman & LaPointe, P.C.

[57] ABSTRACT

The invention provides a method for inhibiting protein isoprenylation by administration of a polyisoprenyl pyrophosphate analogue. The polyisoprenyl pyrophosphate analogue may have formula 1,

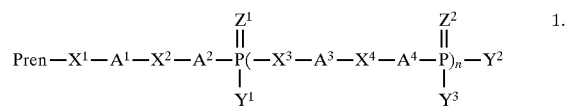

wherein:
Pren represents a $C_{10}$–$C_{30}$ terpenoid group or a derivative thereof;
$A^1$, $A^2$, $A^3$ and $A^4$ independently represent a direct bond or a $C_1$–$C_4$ alkylene or alkenylene group, optionally having substituents selected from methyl, hydroxy, methoxy, mercapto, methylthio, amino, methylamino, dimethylamino, halogen and a group having formula —$X^5$—$A^5$—$P(=Z^2)$ $Y^2Y^3$; $A^5$ represents a direct bond or a $C_1$–$C_4$ alkylene or alkenylene group;
$X^1$, $X^2$, $X^3$, $X^4$ and $X^5$ independently represent a direct bond, oxygen, sulphur, imino or methylimino;
$Y^1$, $Y^2$ and $Y^3$ independently represent hydroxy, alkoxy, mercapto, alkylthio, amino, mono- or di-alkylamino, alkyl, alkenyl, alkynyl, cycloalkyl, aryl or arylalkyl, whereby one of $Y^1$, $Y^2$ and $Y^3$ may also represent a $C_7$–$C_{30}$ alkyl or alkenyl group or a group having formula —$X^5$—$A^5$—P $(=Z^2)Y^2Y^3$ and two of $Y^1$, $Y^2$ and $Y^3$ may together represent an oxygen or sulfur atom or an imino or methylene group;
$Z^1$ and $Z^2$ independently represent oxygen or sulphur; and n is 0, 1 or 2;
or a pharmaceutically acceptable salt thereof.

The invention further provides a pharmaceutical composition containing such a polyisoprenyl pyrophosphate analogue, which composition is suitable for the treatment of carcinomas such as by the inhibition of the isoprenylation of a member of the ras protein family.

16 Claims, 1 Drawing Sheet

METHOD FOR THE TREATMENT OF DISEASES RELATED WITH PROTEIN ISOPRENYLATION

CROSS-REFERENCE TO RELATED APPLICATIONS

The present invention is a Continuation-In-Part of application Ser. No. 07/957,614, filed Oct. 6, 1992 by Louis Hartog Cohen et al, now abandoned.

BACKGROUND OF THE INVENTION

The present invention is in the field of medicine. More specifically, it relates to a novel use of polyisoprenyl pyrophosphate analogues in interfering with certain biochemical processes, in particular to the use of analogues wherein the polyisoprenyl group is farnesyl or geranylgeranyl.

Recently the post-translational modification of mammalian cell proteins involving thioether derivatisation of carboxyl-terminal cysteine residues by mevalonate-derived isoprenyl groups was discovered. Several of these isoprenylated proteins were identified as belonging to groups of related proteins: e.g. the nuclear lamins, low molecular weight GTP binding proteins, such as the rasoncogene proteins and heteromeric G proteins (Schafer et al., Science 245 (1989) 379–385). The polyisoprenyl group that was attached to a protein was identified as either farnesyl ($C_{15}$) or geranylgeranyl ($C_{20}$), probably depending on the recognition of the C-terminal amino acid sequence of the proteins involved. Lamins and $p21^{ras}$ proteins, which possess the consensus CAAX motif (C=cysteine, A=any amino acid having an aliphatic side chain and X=any amino acid), are farnesylated, while several members of the rab proteins having C-terminal CC/CXC motifs, and of the heteromeric G-protein γ-subunits are geranylgeranylated.

The isoprenylation of these proteins seems to play a role in their association with membranes and nuclear envelopes, where they are processed further and/or perform their function. This was shown for example by blocking the mevalonate synthesis by HMG-CoA reductase inhibitors, which prevented proteolytic processing of the lamin A precursor (Beck et al., *J. Cell. Biol.* 110 (1990) 1489–1499) or resulted, in other studies, in the accumulation of non-isoprenylated $p21^{ras}$ precursor and the loss of transforming activity of oncogenic ras proteins. A review of the post-translational modification of proteins by isoprenoids in mammalian cells is given by Maltese W. A. in FASEB J. 4 3319–3329 (1990). The latter observation triggered the search for specific inhibitors of the farnesylation of $p21^{ras}$ in order to prevent its action in cells, where overexpression of this protein leads to tumor development, such as in colon carcinomas.

G proteins play a role in the receptor-mediated transduction of signals (such as growth modulation signals) over the plasma membrane, and other isoprenylated proteins, not yet identified, may have a function in cell cycle progression. There is some evidence as well that GTP binding proteins are involved in the regulation of intracellular protein traffic and secretion. There is even some suggestion that isoprenylated proteins play a role in the translational control of HMG-CoA reductase, the rate limiting enzyme of the isoprene and subsequent cholesterol synthesis.

The enzymes involved in the protein isoprenylation process, isoprenyl: protein transferases, are reported to use all-trans farnesyl pyrophosphate (FPP) as a substrate for the addition of the farnesyl group to the protein. FPP may also be a substrate in the production of geranylgeranyl pyrophosphate, which is subsequently used in the synthesis of geranylgeranylated proteins.

It is known that farnesyl pyrophosphate is a substrate in a key step in the synthesis of cholesterol. In this step the synthesis of squalene from farnesyl pyrophosphate is effected by the enzyme squalene synthase. In this step squalene is formed by formation of a bond between two farnesyl groups in a reaction that requires a synthase. In EP-A-324421 and EP-A-356886 certain farnesyl pyrophosphate analogues have been described that can be used for inhibiting said step in cholesterol synthesis, for use in the treatment of hypercholesterolaemia. Such a process differs from the protein isoprenylation in which other enzymes are required for the isoprenylation, e.g. farnesylation or geranylgeranylation of proteins.

SUMMARY OF THE INVENTION

It is an object of the present invention to provide methods and means for inhibiting protein isoprenylation, in order to prevent or inhibit undesired biological processes such as tumor development.

This object is achieved by using a polyisoprenyl pyrophosphate analogue for preparing a pharmaceutical composition suitable for inhibiting protein isoprenylation.

In an embodiment of the invention, the analogue includes the use of specific polyisoprenyl pyrophosphate analogues having formula 1,

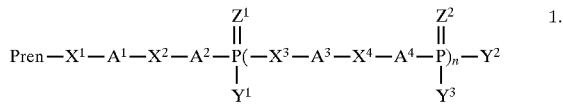

wherein:
Pren represents a $C_{10}$–$C_{30}$ terpenoid group or a derivative thereof; $A^1, A^2, A^3, A^4$ independently represent a direct bond or a $C_1$–$C_4$ alkylene or alkenylene group, optionally having substituents selected from methyl, hydroxy, methoxy, mercapto, methylthio, amino, methylamino, dimethylamino, halogen and a group having formula —$X^5$—$A^5$—P(=$Z^2$)$Y^2Y^3$; $A^5$ represents a direct bond or a $C_1$–$C_4$ alkylene or alkenylene group;
$X^1, X^2, X^3, X^4$, and $X^5$ independently represent a direct bond, oxygen, sulphur, imino or methylimino, with the proviso that if $A^1$ represents a direct bond, $X^2$ also represents a direct bond and vice versa, and if $A^3$ represents a direct bond, $X^4$ also represents a direct bond and vice versa;
$Y^1, Y^2$ and $Y^3$ independently represent hydroxy, alkoxy, mercapto, alkylthio, amino, mono- or di-alkylamino, alkyl, alkenyl, alkynyl, cycloalkyl, aryl or arylalkyl, wherein alkyl, alkoxy, alkenyl and alkynyl are linear or branched having 1–6 carbon atoms and may have substituents selected from hydroxy, methoxy, mercapto, methylthio, amino, methylamino, dimethylamino and halogen, cycloalkyl having 3–6 carbon atoms, aryl is carbocyclic or heterocyclic having 5–10 ring atoms and cycloalkyl and aryl may have substituents selected from methyl, hydroxy, methoxy and halogen, whereby one of $Y^1, Y^2$ and $Y^3$ may also represent a $C_{7}$–$C_{30}$ alkyl or alkenyl group, including a $C_{10}$–$C_{30}$ terpenoid group, and $Y^1$ may represent a group having formula —$X^5$—$A^5$—P(=$Z^2$)$Y^2Y^3$ and two of $Y^1, Y^2$ and $Y^3$ may together represent an oxygen or sulphur atom or an imino or methylene group; $Z^1$ and $Z^2$ independently represent oxygen or sulphur; and n is 0, 1 or 2;
or a pharmaceutically acceptable salt thereof; with the proviso that the polyisoprenyl pyrophosphate analogue is not the polyisoprenyl pyrophosphate itself.

BRIEF DESCRIPTION OF THE DRAWINGS

The Figure is a graph representing the inhibition of proliferation of Rat-1.H-ras13 cells for a compound representing an embodiment of the present invention.

DETAILED DESCRIPTION OF THE PREFERRED EMBODIMENT

Figure 1:
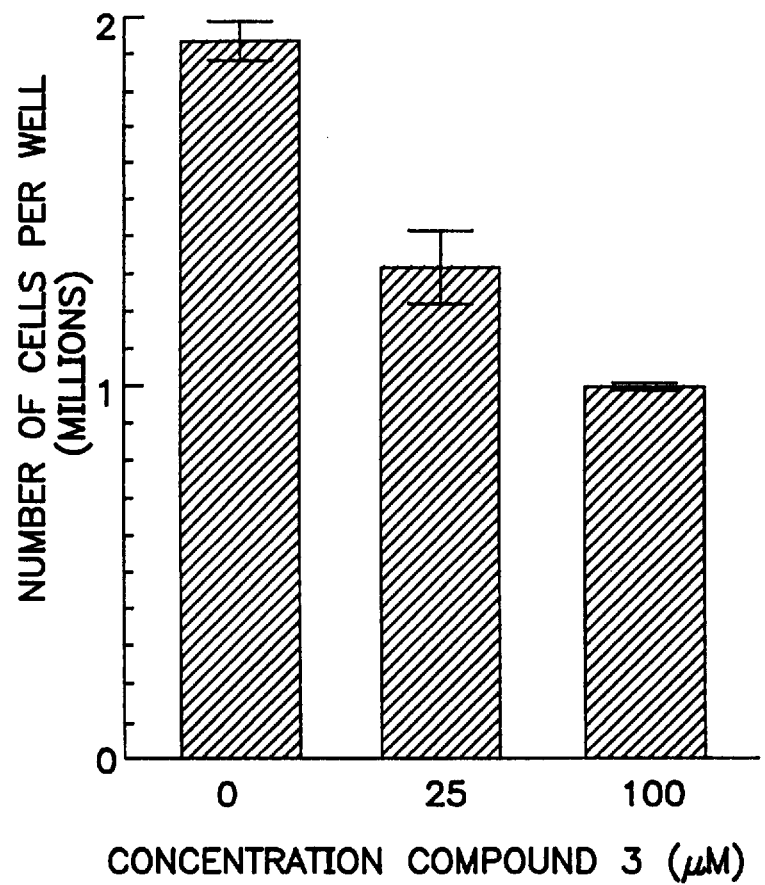

The present invention provides the use of specific polyisoprenyl pyrophosphate analogues having formula 1,

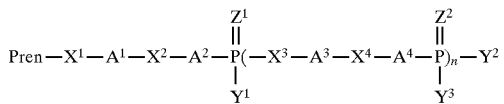

wherein:

Pren represents a $C_{10-C30}$ terpenoid group or a derivative thereof; $A^1, A^2, A^3, A^4$ independently represent a direct bond or a $C_1-C_4$ alkylene or alkenylene group, optionally having substituents selected from methyl, hydroxy, methoxy, mercapto, methylthio, amino, methylamino, dimethylamino, halogen and a group having formula $—X^5—A^5—P(=Z^2)Y^2Y^3$; $A^5$ represents a direct bond or a $C_1-C_4$ alkylene or alkenylene group;

$X^1$, $X^2$, $X^3$, $X^4$, and $X^5$ independently represent a direct bond, oxygen, sulphur, imino or methylimino, with the proviso that if $A^1$ represents a direct bond, $X^2$ also represents a direct bond and vice versa, and if $A^3$ represents a direct bond, $X^4$ also represents a direct bond and vice versa;

$Y^1$, $Y^2$ and $Y^3$ independently represent hydroxy, alkoxy, mercapto, alkylthio, amino, mono- or di-alkylamino, alkyl, alkenyl, alkynyl, cycloalkyl, aryl or arylalkyl, wherein alkyl, alkoxy, alkenyl and alkynyl are linear or branched having 1–6 carbon atoms and may have substituents selected from hydroxy, methoxy, mercapto, methylthio, amino, methylamino, dimethylamino and halogen, cycloalkyl having 3–6 carbon atoms, aryl is carbocyclic or heterocyclic having 5–10 ring atoms and cycloalkyl and aryl may have substituents selected from methyl, hydroxy, methoxy and halogen, whereby one of $Y^1$, $Y^2$ and $Y^3$ may also represent a $C_{7-C30}$ alkyl or alkenyl group, including a $C_{10}-C_{30}$ terpenoid group, and $Y^1$ may represent a group having formula $—X^5—A^5—P(=Z^2)Y^2Y^3$ and two of $Y^1$, $Y^2$ and $Y^3$ may together represent an oxygen or sulphur atom or an imino or methylene group; $Z^1$ and $Z^2$ independently represent oxygen or sulphur; and n is 0, 1 or 2;

or a pharmaceutically acceptable salt thereof; with the proviso that the polyisoprenyl pyrophosphate analogue is not the polyisoprenyl pyrophosphate itself.

In the above formula 1, the group Pren generally represents an acyclic terpenoid group, i.e. a hydrocarbon group consisting of $C_5$ isoprenylene (2-methyl-1,4-but-2-enylene) units, in particular 2–6 of such isoprenylene units. One or more of these isoprenylene units may be replaced by isomeric units such as 2-methyl-1,2-but-3-enylene or 2-methylene-1,4-butylene. The C—C double bond in these units may be cis and/or trans, but is preferably trans. One or more of the double bonds may be hydrogenated resulting in a terpenoid group having less than one double bond per $C_5$ moiety, or alternatively one or more of the single C—C bonds may be dehydrogenated resulting in a terpenoid group having more than one double bond per $C_5$, moiety. Preferably the terpenoid group contains one C—C double bond per $C_5$, moiety. The terpenoid group may be substituted e.g. by halogen, in particular fluorine, methoxy or additional methyl; on the other hand one or more methyl side groups may be lacking. Preferably the terpenoid group is a $C_{10}–C_{20}$ group (monoterpenic, sesquiterpenic or diterpenic). Examples of monoterpenic groups $(C_{10})$ are geranyl, neryl, linalyl, ocimenyl, myrcenyl and citronellyl. Examples of sesquiterpenic groups are α-farnesyl, β-farnesyl, nerolidyl and dihydro derivatives thereof. Examples of diterpenic groups are geranyl-geranyl, geranyl-linalyl and hydrogenated derivatives thereof such as geranyl-citronellyl and phytyl. Preferred terpenoid groups are farnesyl and geranyl-geranyl. Most preferred is all-trans-α-polyisoprenyl.

The two groups represented by $X^1—A^1—X^2—A^2$ and $X^3—A^3—X^4—A^4$ in formula 1 are in particular each a direct bond between the terpenoid group and the phosphorus atom or a heteroatom such as oxygen, nitrogen or sulphur, or an alkylene group, or an alkylene group flanked by one or two heteroatoms or a heteroatom flanked by two alkylene groups. The heteroatom is preferably oxygen or sulphur, most preferably oxygen. The alkylene group may have substituents such as fluorine, chlorine, methyl, hydroxy or methoxy, and it is preferably methylene. The group $X^1—A^1—X^2—A^2$ is more in particular a direct bond, a methylene group, an oxymethylene group, a methyleneoxy group or a substituted methylene, oxymethylene or methyleneoxy group. The group $X^3—A^3—X^4—A^4$ is more in particular an oxygen atom, a methylene group, a methyleneoxy group or a substituted methylene or methyleneoxy group. The multiplicator n may have a value of 0, 1 or 2, representing for example monophosphonates, pyrophosphates (diphosphonates), and triphosphates respectively, but is preferably 1.

In another preferred group of polyisoprenyl pyrophosphate analogues, the carbon-phosphorus chain is branched. Such analogues have formula 1, wherein at least one of $A^1$, $A^2$, $A^3$ and $A^4$, and preferably $A^1$ is alkylene, especially methylene, which is substituted by a group having formula $—X^5—A^5—P(=Z^3)Y^2Y^3$. Preferably, $A^2$ and $A^5$ independently represent a direct bond or alkylene, especially methylene, $X^1$, $X^2$ and $X^5$ independently represent a direct bond or oxygen, and n=0. Alternatively, a phosphono substituent may be present on the α-carbon atom of the isoprenyl group.

The groups $Y^1$, $Y^2$ and $Y^3$ in formula 1 preferably comprise one or more hydrophilic groups, such as hydroxy, hydroxyethyl, mercapto or amino. In particular, at least one of $Y^1$, $Y^2$ and $Y^3$, and more in particular at least two of $Y^1$, $Y^2$ and $Y^3$ are hydroxy, mercapto or salts thereof; the remaining ones may for example be methyl, ethyl, phenyl, benzyl, methoxy, farnesyloxy, phenoxy, cyclohexyloxy, methylthio, dimethylamino, or preferably a group having formula $—X^5—A^5—P(=Z^2)Y^2Y^3$; etc. Also, $Y^1$ and $Y^2$ or $Y^1$ and $Y^3$ may be connected to each other, e.g. as a cyclic phosphoric diester or a cyclic phosphonate. Where any of $Y^1$, $Y^2$ and $Y^3$ represents hydroxy or mercapto, the resulting phosphoric, phosphonic or phosphinic acid may be in the form of a pharmaceutically acceptable salt, e.g. an ammonium, substituted ammonium, alkali metal or alkaline earth metal salt. Preferred compounds are those wherein $Y^1$, $Y^2$ and $Y^3$ each represent hydroxy or mercapto, preferably hydroxy, and in particular the salts thereof.

The groups $Z^1$ and $Z^2$ in formula 1 are oxygen or sulphur, preferably oxygen.

Examples of polyisoprenyl pyrophosphate analogues to be used according to the invention include farnesylmethylphosphono-phosphate $(C_{15}H_{25}—CH_2—PO(OH)—O—PO(OH)_2)$ (1) $(C_{15}H_{25}=\text{farnesyl})$, farnesylmethylphosphono-methylphosphonate $(C_{15}H_{25}—CH_2—PO(OH)—O—PO(OH)CH_3)$ (2), farnesylphosphono-phosphate $(C_{15}H_{25}—PO(OH)—O—PO(OH)_2$ (3), farnesylphosphono-methylphosphonate $(C_{15}H_{25}-PO(OH)-O-PO(OH)CH_3)$ (4), farnesyloxymethylphosphono-phosphate $(C_{15}H_{25}-O-CH_2-PO(OH)-O-PO(OH)_2)$ (5), farnesyl(phosphono)methoxymethylphosphonic acid $(C_{15}H_{25}-OH(PO(OH)_2)-O-CH_2-PO(OH)_2$ (6), ($\alpha$-phosphonofarnesyl)oxymethylphosphinic acid $(C_{14}H_{23}-CH(PO(OH)_2)-O-CH_2-PO(OH)_2$ (7), farnesylphosphonoylbis(methylenephosphonic acid) $(C_{15}H_{25}-PO(CH_2-PO(OH)_2)_2$ or its cyclic anhydride 5-farnesyl-1,3-dihydroxy-2-oxa-1,3,5-triphosphinane-1,3,5-trione, farnesyloxymethylphosphonoylbis-(methylphosphonic acid) $(C_{15}H_{25}-O-CH_2-PO(CH_2-PO(OH)_2)_2$ or its cyclic anhydride 5-farnesyloxymethyl-1,3-dihydroxy-2-oxa-1,3,5-triphosphinane-1,3,5-trione, farnesyl(phosphono)methylphosphonomethylphosphonic acid $(C_{15}H_{25}-CH(PO(OH)_2)-PO(OH)-CH_2-PO(OH)_2$ or its cyclic anhydride 4-farnesyl-1,3,5-trihydroxy-2-oxa-1,3,5-triphosphinane-1,3,5-trione, and farnesylthiophosphonophosphate $(C_{15}H_{25}-PS(OH)-O-PO(OH)_2)$ and the corresponding geranylgeranyl compounds and the corresponding cyclic anhydrides thereof, with a preference for compounds (1) and (3).

The polyisoprenyl pyrophosphate analogues to be used according to the invention can be prepared in a manner which is known per se. For example, they may be prepared by the method described by Valentijn et al., *Synlett*, 1991, 663–664, or by the methods described in European patent applications 324421 and 356866.

Surprisingly it was found that the polyisoprenyl pyrophosphate analogues according to the invention are capable to specifically inhibit the protein isoprenylation at low dosage amounts ($IC_{50}<1$ $\mu$M) and that squalene synthesis is not inhibited significantly at these dosage amounts, i.e. squalene synthesis is inhibited less than 10%, preferably less than 2% at the $IC_{50}$ for protein isoprenylation inhibition. Preferably the FPP analogue concentration will be selected in order to disturb other processes which use FPP or similar substrates, e.g. the squalene synthesis, as little as possible. Therefore, preferred FPP analogues to be used according to the invention are analogues that are specific for the isoprenylation reaction to be inhibited.

For example the compounds (1) and (3) mentioned above can inhibit $p21^{ras}$; farnesyl transferase when applied in dosage amounts that are too small for said analogues to inhibit squalene synthase, thereby inhibiting farnesylation of $p21^{ras}$ without inhibiting squalene synthesis.

The polyisoprenyl pyrophosphate analogues described above are useful as an active substance in a pharmaceutical composition intended to interfere with protein isoprenylation. As such, they are useful as inhibitors in processes such as oncogenesis and other unwanted cell proliferation, and furthermore as suppressants of aberrant high signal transduction.

The pharmaceutical compositions to be prepared using the polyisoprenyl pyrophosphate analogues according to the invention may be formulated in a usual way, e.g. by associating the polyisoprenyl pyrophosphate analogue with a suitable solid or liquid carrier and optional adjuvants or other active components. The composition may be suitable for oral administration (capsule, pill, tablet, gel, powder, sachet, syrup, solution, dispersion etc.) or may be an injectable solution or another administration form. The composition may be administered to mammalians including man, in a dose which depends on the particular purpose of the administration, the body weight and other conditions well known to the skilled person. A dose can be administered in a single dosage or in several daily dosages.

The invention also concerns a method for the prophylaxis, and especially the treatment, of diseases related to protein isoprenylation by administration of a polyisoprenyl pyrophosphate analogue as described above in a dose which is effective for inhibiting protein isoprenylation. In particular the method of the invention is directed at the prophylaxis and/or treatment of carcinomas, such as by the inhibition of the isoprenylation of a member of the ras protein family, in particular $p21^{ras}$.

EXAMPLE 1

Preparation of farnesylmethylphosphonophosphate (1)

Methyl methylphosphonomorpholidate (a)

Methyl phosphonic dichloride (6.65 g, 50 mmol) was dissolved in freshly distilled ether (80 ml) and cooled to 0° C. Then morpholine (8.72 ml, 100 mmol) in 20 ml ether was added dropwise over a period of 2 h and stirring was continued overnight at 0° C. The salts were removed by filtration and the solvent was evaporated. The residue was dissolved in 50 ml ether and treated with a mixture of methanol (3.82 ml, 100 mmol) and triethylamine (6.97 ml, 50 mmol) in 50 ml ether at 0° C. After overnight stirring at 0° the salts were removed by filtration, followed by concentration. Compound (a) was purified by distillation (bp. 118° C. at 0.7 mm Hg) and obtained in a yield of 79%.

$^{13}$C NMR (CDCl$_3$)$\delta$ (ppm) 7.9, 10.8 (CH$_3$, J$_{cp}$=144.9 Hz); 43.4 (CH$_2$); 51.6, 51.7 (OCH$_3$); 66.7 (CH$_2$).

$^{31}$P NMR (CDCl$_3$)$\delta$ 32.8

Farnesyl chloride (b)

N-Chlorosuccinimide (0.66 g, 4.95 mmol) was dissolved in 20 ml of dry CH$_2$Cl$_2$ under a nitrogen atmosphere. The solution was cooled to −30° C. and 0.37 ml dimethyl sulphide (5 mmol) was added. The mixture was allowed to warm to 0° C. before it was cooled to −40° C. Then farnesol (1 g, 4.5 mmol) dissolved in 2.5 ml CH$_2$Cl$_2$ was added dropwise to the mixture over a period of 3 minutes. The reaction mixture was warmed to 0.C in 1 h, at which temperature it was maintained for another hour. After 15 minutes of stirring at room temperature the reaction mixture was poured into a separatory funnel which contained 12.5 ml of cold saturated NaCl. The aqueous layer was extracted with two 10 ml portions of pentane. The organic layers were combined with an additional 10 ml of pentane and washed with two 5 ml portions of cold saturated NaCl. The organic layer was dried over MgSO$_4$ and concentrated to dryness in vacuo. Compound (b) was thus obtained in a yield of 89%.

$^{13}$C NMR (CDCl$_3$) $\delta$ 16.0, 17.6, 25.7 (4×CH$_3$); 26.1, 26.7, 39.4, 39.7 (C4, C5, C7, C8); 41.1 (C1); 120.3, 124.0, 124.3 (C2, C6, C10); 130.3, 135.5 (C3, C7, C9).

$^1$H NMR (CDCl$_3$) $\delta$ 1.60 (s, 6H, 2×CH$_3$); 1.68 (s, 3H, CH$_3$); 2.01–2.35 (m, 8H, H$_4$, H$_5$, H$_8$, H$_9$); 4.07, 4.11 J$_{1,2}$=8 Hz (d, 2H, H$_1$); 7.15–7.29 (m, 3H, H$_2$, H$_6$, H$_{10}$)

Hf: 0.64 (ether/light petroleum 1/1 v/v).

Farnesylmethyl-methylphosphonomorpholidate (c)

Compound (a) (376 mg 2.1 mmol) was dissolved in 10 ml freshly distilled THF and cooled to −78° C. under an argon atmosphere. Then 1.3 ml n-butyl-lithium (1.6M in hexane, 2.1 mmol) was added and stirring was continued for 20 minutes, followed by dropwise addition of compound (b) (481 mg, 2 mmol) in 5 ml THF over a period of 5 minutes. After additional stirring for 1 h at −78° C., work-up and chromatographical purification, the desired compound (c) was obtained as a colorless oil in a yield of 63%.

$^{13}$C NMR (CDCl$_3$) $\delta$ 15.9, 17.5, 25.6 (4×CH$_3$); 20.7, 20.8 (C2); 23.4, 26.1 (C1); 26.3, 26.6 (C5, C9); 39.4, 39.6 (C5, C10); 52.0, 52.1 (2×OCH$_3$); 122.6, 122.9 (C3); 123.8, 124.9 (C7,C11); 131.0, 134.9, 136.4 (C4, C8, C12).

$^1$H NMR (CDCl$_3$) δ 1.58 (s, 6H, 2×CH$_3$), 1.62 (s, 3H, CH$_3$), 1.68 (s, 3H, CH$_3$), 1.71–1.82 (m, 2H, H$_1$); 1.97–2.09 (m, 8H, H$_5$, H$_8$, H$_9$, H$_{10}$); 2.23–2.34 (m, 2H, H$_3$); 3.72, 3.76 (2×s, 6H, 2×OCH$_3$); 5.07–5.30 (m, 3H, H$_3$, H$_7$, H$_{12}$).
$^{31}$P NMR (CDCl$_3$) δ 33.0.
Rf 0.17 (5% acetone in dichloromethane)

Farnesylmethylphosphonomorpholidate (d)

Compound (c) (383 mg. 1 mmol) was coevaporated three times with toluene and dissolved in 2 ml dry acetonitrile. Then trimethylsilyl bromide (1.1 mmol) was added. As $^{31}$P NMR (δ 27.9) showed that the reaction had gone to completion the reaction mixture was concentrated and treated with 1 ml of a 1M solution of tetrabutylammonium fluoride in dry dioxane. Again $^{31}$P NMR showed that the reaction was complete (δ 20.0), and compound (d) was obtained, which was not isolated, but used in the next step without purification.

Farnesylmethylphosphonophosphate (1).

Compound (d) was dissolved in 3 ml dry pyridine and 3 mmol tributylammonium phosphonic acid was added. Following evaporation of the solvent, the mixture was redissolved in dry pyridine and stirred for two days at room temperature. Then the reaction mixture was concentrated to dryness, dissolved in a small amount of 2-propanol/0.15M NH$_4$HCO$_3$ (1/49 v/v) and applied to a Dowex 50 W×4 cation exchange resin (NH$_4^+$form). After elution with the same solvent the eluate was concentrated to dryness. Purification was accomplished by gel filtration on a High Load 26/60 Sephacryl S-100 High Resolution column, eluting with a solution of 30% methanol in 0.15M NH$_4$HCO$_3$. After lyophilization of the appropriate fractions compound (1) was obtained as a white powder in a yield of 65%.
$^1$H NMR (CD$_3$OD) δ 1.59 (s, 6H, 2×CH$_2$); 1.65, 1.66 (2x, s, 6H, 2×CH$_3$); 1.99–2.16 (m, 10H, H$_1$, H$_5$, H$_8$, H$_9$, H$_{10}$); 2.28–2.39 (m, 2H, H$_2$); 5.17–5.29 (m, 3H, H$_3$, H$_7$, H$_{12}$).
$^{31}$P NMR (D$_2$O) δ −9.8, −9.5, 16.4, 16.7 (J$_{pp}$=26.3 Hz).

EXAMPLE 2

The inhibition of the farnesylation of p2$^{ras}$ precursor by the enzyme farnesyl; protein transferase present in rabbit reticulocyte lysate by farnesylmethylphosphonophosphate (compound 1) and farnesylphosphonophosphate (compound 3) was tested. The prenylation of bacterially expressed, unprocessed H-ras protein (30 μg/ml) was determined in untreated reticulocyte lysate (Promega) using 1 μM of [$^3$H]-farnesyl pyrophosphate (ARC Inc.; 15 Ci/mmol), 1 mM MgCl$_2$ and 1 mM DTT. The incubations were conducted at 37° C. for 30 min in the presence of different amounts of compound 1 or 3. Final incubation volume was 25 μl. The incorporation of [$^3$H]-FPP into TCA precipitable material was determined as described by Reiss et al., *Cell* 62 (1990) 81–88. The difference between the values obtained in the presence of ras-protein and those obtained without this addition (blank) was a measure for the remaining enzyme activity. This activity was concentration-dependently decreased by both compounds. From the dose-response curve the IC$_{50}$ values were calculated, which were 4 μM and <1 μM for compound 1 and 3, respectively.

Inhibition of the same enzyme (protein;farnesyl transferase) was also tested using the C-terminal octapeptide pre-p21$^{N-ras}$ coupled to Sepharose beads as substrate in the enzyme assay instead of the whole p21$^{ras}$ precursor protein. The IC$_{50}$ values were 0.93±0.23 μM for compound (1), 0.34±0.05 μM for compound (3), 0.52±0.07 μM for compound (5), 0.58±0.44 μm for compound (6) and 1.08±0.23 μM for compound (7). As a comparison, bisfarnesylmethylenebis(phosphonic acid), a compound which is not according to the invention, has an IC$_{50}$ value of 147±37 μM.

Similarly the IC$_{50}$-values were obtained for the compounds 1 and 3 respectively for inhibition of the enzyme squalene synthase in rat liver microsomal preparations. The IC$_{50}$-values were 480 μM and 120 μM respectively.

EXAMPLE 3

Inhibition of the farnesylation of p21$^{ras}$ by farnesylphosphonophosphate (compound 3) in Rat-1.H-ras13 cells in culture.

It was shown now that compound 3 acts as a protein: farnesyl transferase inhibitors in cultured cells. For this purpose Rat-1.H-ras13 cells, which overexpress human p21$^{Ha-ras}$ (Downword J. et al., Proc. Natl. Acad. Sci. U.S.A. 1988; 85; 5774–5778), were used. These cells were incubated with [$^3$H]-mevalonate and 0, 0.1, 1, 10 and 100 μM of compound 3 for 24 h in DMEM containing 1% human serum albumin and 2.5 μM of simvastatin.

Thereafter cells were lysed in 300 μl PBS supplemented with 1% Triton X-100, 0.5% sodium deoxycholate, and the protease inhibitors phenylmethylsulfonylfluoride (1 mM), leupeptine (50 μg/ml), pepstatin A (50 μg/ml) and trasylol (300 K.I.U./ml), and p21$^{ras}$ was collected on immobilized monoclonal antibody Y13–259 (Osterop A.P.R.M. et al., J. Biol. Chem. 1992; 267; 14647–14653). After separation by SDS polyacrylamide gel electrophoresis the [$^3$H]-labelled polypeptides were visualized by autoradiography.

It was observed that with increasing concentrations of compound 3 less radioactivity was incorporated into p21$^{ras}$. The IC$_{50}$ value was found to be in between 1 and 10 μM. At 100 μM of compound 3, no radioactivity was measured, showing that the farnesylation of the ras protein was totally blocked.

These experiments confirm that the farnesylation of p21$^{Ha-ras}$ in these cells is inhibited in vivo by farnesyl phosphonophosphate (compound 3).

Mutation in human Ras-protein leads to cell transformation. It has been shown that inhibition of farnesylpyrophosphate production, preventing the farnesylation of Ras, blocked the in vivo biological activity of mutated human Ras proteins (Schafer et al., Science 1989; 245; 379–385); Jackson et al., Proc. Natl. Acad. Sci. U.S.A. 1990; 87; 3042–3046).

Therefore, it is to be expected that compound 3, which inhibits the farnesylation of Ras-protein in cell culture as shown above, will prevent cell transformation in case the Ras-protein has been mutated.

EXAMPLE 4

Inhibition of cell proliferation of transformed Rat-1,H-ras13 cells by farnesylphosphonophosphate (compound 3).

It was shown that compound 3, probably as a consequence of inhibition of ras farnesylation, is able to block the growth of these cells in culture. The experiment was performed as follows:

Cells were cultured for 10 days in DMEM supplemented with 10% fetal calf serum in the presence of 0, 25 or 100 μM of compound 3. At day 0, cells were plated in monolayer culture at 5×10$^3$ cells per well (6 well plates). On day 3 and 7, cells were re-fed with the same medium. On day 10, cells were harvested by trypsinization and counted using a standard hemocytometer chamber. Values are the mean of triplicate countings of duplicate incubations. In these ten days control cells had been proliferated exponentially to 1.94× 10$^6$±0.04×10$^6$ cells per well. As shown in the Figure, which represents the inhibition of proliferation of Rat-1.H-ras13 cells by compound 3, incubation with 25 and 100 μM of compound 3 led to a reduction in cell numbers of 32.5 and 49.5% of control values, respectively. In all cases no non-viable cells, as determined by the trypan blue exclusion method, were observed.

These results show that compound 3 concentration-dependently inhibits the proliferation of transformed cells in culture, which is expected for a compound that inhibits the farnesylation of ras-protein (see e.g. Kohl et al., Science 260 (1993) 1934–1937; James et al., Science 260 (1993) 1937–1941).

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A pharmaceutical composition in the form of a pharmaceutical carrier selected from the group consisting of a capsule, pill, tablet, gel, powder, sachet, syrup, dispersion, and an injectable solution and an effective amount of a protein isoprenylation inhibiting compound including polyisoprenyl pyrophosphate analogue having formula 1,

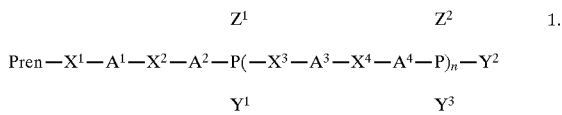

wherein:
Pren represents a member from the group consisting of $C_{10}$–$C_{30}$ terpenoid group and isomerised, hydrogenated, dehydrogenated, α-phosphono-substituted, halogen-substituted, methoxy-substituted, methyl-substituted and demethylated derivatives thereof;
$A^1$, $A^2$, $A^3$ and $A^4$ independently represent a direct bond or a $C_1$–$C_4$ alkylene or alkenylene group, optionally having substituents selected from methyl, hydroxy, methoxy, mercapto, methylthio, amino, methylamino, dimethylamino, halogen and a group having formula —$X^5$—$A^5$—P(=$Z^2$)$Y^2Y^3$; $A^5$ represents a direct bond or a $C_1$–$C_4$ alkylene or alkenylene group;
$X^1$, $X^2$, $X^3$, $X^4$ and $X^5$ independently represent a direct bond, oxygen, sulphur, imino or methylimino, with the proviso that if $A^1$ represents a direct bond, $X^2$ also represents a direct bond and vice versa, and if $A^3$ represents a direct bond, $X^4$ also represents a direct bond and vice versa;
$Y^1$, $Y^2$ and $Y^3$ independently represent hydroxy, alkoxy, mercapto, alkylthio, amino, mono- or di-alkylamino, alkyl, alkenyl, alkynyl, cycloalkyl, aryl or arylalkyl, wherein alkyl, alkoxy, alkenyl and alkynyl are linear or branched having 1–6 carbon atoms and may have substituents selected from hydroxy, methoxy, mercapto, methylthio, amino, methylamino, dimethylamino and halogen, cycloalkyl has 3–8 carbon atoms, aryl is carbocyclic or heterocyclic having 5–10 ring atoms and cycloalkyl and aryl may have substituents selected from methyl, hydroxy, methoxy and halogen, whereby one of $Y^1$, $Y^2$ and $Y^3$ may also represent a $C_7$–$C_{30}$ alkyl or alkenyl group, including a $C_{10}$–$C_{30}$ terpenoid group, $Y^1$ may represent a group having formula —$X^5$—$A^5$—P(=$Z^2$)$Y^2Y_3$ and two of $Y^1$, $Y^2$ and $Y^3$ may together represent an oxygen or sulphur atom or an imino or methylene group;
$Z^1$ and $Z^2$ independently represent oxygen or sulphur; and n is 0, 1 or 2;

or a pharmaceutically acceptable salt thereof; with the proviso that the polyisoprenyl pyrophosphate analogue is not polyisoprenyl pyrophosphate itself.

2. Composition according to claim 1, wherein Pren represents a farnesyl or geranyl-geranyl group, or an α-phosphono-substituted derivative thereof.

3. Composition according to claim 1, wherein $A^1$ and $A^3$ independently represent a direct bond, a methylene group or a methylene group substituted with a group having formula —$X^5$—$A^5$—P(=$Z^2$)$Y^2Y^3$; at least two of $Y^1$, $Y^2$ and $Y^3$ are hydroxy or mercapto or a salt thereof; and n=0 or 1.

4. Composition according to claim 3, wherein the polyisoprenyl pyrophosphate analogue has formula 1, wherein Pren represents a farnesyl or geranyl-geranyl group or an α-phosphono-substituted derivative thereof, $A^1$ represents a group having formula >CH—$X^5$—$A^5$—P(=$Z^2$)$Y^2Y^3$, $A^2$ and $A^5$ independently represent a direct bond or methylene, $X^1$, $X^2$ and $X^5$ independently represent a direct bond or oxygen, $Y^1$, $Y^2$ and $Y^3$ each represent hydroxy or mercapto or a salt thereof, $Z^1$ and $Z^2$ each represent oxygen or sulfur, and n=0.

5. Composition according to claim 3, wherein the polyisoprenyl pyrophosphate analogue has formula 1, wherein Pren represents a farnesyl or geranyl-geranyl group, $X^1$—$A^1$—$X^2$—$A^2$ together represent a direct bond, methylene, oxymethylene or methyleneoxy, $X^3$—$A^3$—$X^4$—$A^4$ together represent oxygen, methylene, oxymethylene or methyleneoxy, $Y^1$ and $Y^3$ each represent hydroxy or mercapto or a salt thereof, $Y^2$ represents hydroxy or mercapto or a salt thereof, or methyl, $Z^1$ and $Z^2$ each represent oxygen or sulfur, and n=1.

6. Composition according to claim 4, wherein Pren represents farnesyl, $X^1$—$A^1$—$X^2$—$A^2$ together represent a direct bond, oxymethylene or methylene, $X^3$—$A^3$—$X^4$—$A^4$ together represent oxygen or methylene, $Y^1$, $Y^2$ and $Y^3$ each represent hydroxy or a salt thereof, $Z^1$ and $Z^2$ each represent oxygen.

7. Composition according to claim 5, wherein $X^3$—$A^3$—$X^4$—$A^4$ together represent oxygen.

8. Composition according to claim 6, wherein $X^1$—$A^1$—$X^2$—$A^2$ together represent a direct bond, the polyisoprenyl pyrophosphate analogue being farnesylphosphonophosphate.

9. A method for the treatment of a tumor condition wherein the tumor is sensitive to treatment with the composition set out below, which includes the step of administering to a mammal suffering from said condition, a pharmaceutical composition in the form of a pharmaceutical carrier selected from the group consisting of a capsule, pill, tablet, gel, powder, sachet, syrup, solution, dispersion, and an injectable solution and an effective amount of a protein isoprenylation inhibiting compound including a polyisoprenyl pyrophosphate analogue having formula 1,

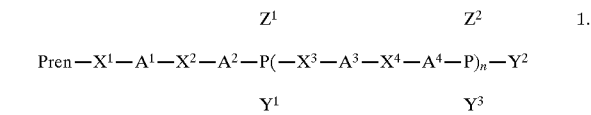

wherein:
Pren represents a member from the group consisting of $C_{10}$–$C_{30}$ terpenoid group and isomerised, hydrogenated, dehydrogenated, α-phosphono-substituted, halogen-substituted, methoxy-substituted, methyl-substituted, and demethylated derivatives thereof;
$A^1$, $A^2$, $A^3$ and $A^4$ independently represent a direct bond or a $C_1$–$C_4$ alkylene or alkenylene group, optionally having substituents selected from methyl, hydroxy, methoxy, mercapto, methylthio, amino, methylamino, dimethylamino, halogen and a group having formula $-X^5-A^5-P(=Z^2)Y^2Y^3$; $A^5$ represents a direct bond or a $C_1-C_4$ alkylene or alkenylene group;

$X^1$, $X^2$, $X^3$, $X^4$ and $X^5$ independently represent a direct bond, oxygen, sulphur, imino or methylimino, with the proviso that if $A^1$ represents a direct bond, $X^2$ also represents a direct bond and vice versa, and if $A^3$ represents a direct bond, $X^4$ also represents a direct bond and vice versa;

$Y^1$, $Y^2$ and $Y^3$ independently represent hydroxy, alkoxy, mercapto, alkylthio, amino, mono- or di-alkylamino, alkyl, alkenyl, alkynyl, cycloalkyl, aryl or arylalkyl, wherein alkyl, alkoxy, alkenyl and alkynyl are linear or branched having 1–6 carbon atoms and may have substituents selected from hydroxy, methoxy, mercapto, methylthio, amino, methylamino, dimethylamino and halogen, cycloalkyl has 3–8 carbon atoms, aryl is carbocyclic or heterocyclic having 5–10 ring atoms and cycloalkyl and aryl may have substituents selected from methyl, hydroxy, methoxy and halogen, whereby one of $Y^1$, $Y^2$ and $Y^3$ may also represent a $C_7-C_{30}$ alkyl or alkenyl group, including a $C_{10}-C30$ terpenoid group, and $Y^1$ may represent a group having formula $-X^3-A^5-P(=Z^2)Y^2Y^3$ and two of $Y^1$, $Y^2$ and $Y^3$ may together represent an oxygen or sulphur atom or an imino or methylene group; $Z^1$ and $Z^2$ independently represent oxygen or sulphur; and n is 0, 1 or 2;

or a pharmaceutically acceptable salt thereof; with the proviso that the polyisoprenyl pyrophosphate analogue is not polyisoprenyl pyrophosphate itself.

10. Method according to claim 8, wherein the polyisoprenyl pyrophosphate analogue has formula 1, wherein Pren represents a farnesyl or geranyl-geranyl group, $X^1-A^1-X^2-A^2$ together represent a direct bond, methylene, oxymethylene or methyleneoxy, $X^3-A^3-X^4-A^4$ together represent oxygen, methylene, oxymethylene or methyleneoxy, $Y^1$ and $Y^3$ each represent hydroxy or mercapto or a salt thereof, $Y^2$ represents hydroxy or mercapto or a salt thereof or methyl, $Z^1$ and $Z^2$ each represent oxygen or sulfur, and n=1.

11. Method according to claim 9, wherein Pren represents farnesyl, $X^1-A^1-X^2-A^2$ together represent a direct bond, oxymethylene or methylene, $X^3-A^3-X^4-A^4$ together represent oxygen or methylene, $Y^1$, $Y^2$ and $Y^3$ each represent hydroxy or a salt thereof, $Z^1$ and $Z^2$ each represent oxygen.

12. Method according to claim 10, wherein $X^3-A^3-X^4-A^4$ together represent oxygen.

13. Method according to claim 11, wherein $X^1-X^2-A^2$ together represent a direct bond, the polyisoprenyl pyrophosphate analogue being farnesylphosphono-phosphate.

14. Method according to claim 8 for the treatment of carcinomas.

15. Method according to claim 8 for the inhibition of the isoprenylation of a member of the ras protein family.

16. Method according to claim 8, wherein the polyisoprenyl pyrophosphate analogue has formula 1, wherein Pren represents a farnesyl or geranyl-geranyl group or an α-phosphono-substituted derivative thereof, $A^1$ represents a group having formula $>CH-X^5-A^5-P(=Z^2)Y^2Y^3$, $A^2$ and $A^5$ independently represent a direct bond or methylene, $X^1$, $X^2$ and $X^5$ independently represent a direct bond or oxygen, $Y^1$, $Y^2$, and $Y^3$ each represent hydroxy or mercapto or a salt thereof, $Z^1$ and $Z^2$ each represent oxygen or sulfur, and n=0.

* * * * *

UNITED STATES PATENT AND TRADEMARK OFFICE
CERTIFICATE OF CORRECTION

PATENT NO. : 5,827,838
DATED : October 27, 1998
INVENTOR(S) : LOUIS HARTOG COHEN ET AL.

It is certified that error appears in the above-identified patent and that said Letters Patent is hereby corrected as shown below:

In Column 9, claim 1, the formula should read as follows:

$$\text{Pren-}X^1-A^1-X^2-A^2-\underset{\underset{Y^1}{|}}{\overset{\overset{Z^1}{\|}}{P}}(-X^3-A^3-X^4-A^4-\underset{\underset{Y^3}{|}}{\overset{\overset{Z^2}{\|}}{P}})_n-Y^2$$

In Column 10, claim 9, the formula should read as follows:

$$\text{Pren-}X^1-A^1-X^2-A^2-\underset{\underset{Y^1}{|}}{\overset{\overset{Z^1}{\|}}{P}}(-X^3-A^3-X^4-A^4-\underset{\underset{Y^3}{|}}{\overset{\overset{Z^2}{\|}}{P}})_n-Y^2$$

UNITED STATES PATENT AND TRADEMARK OFFICE
CERTIFICATE OF CORRECTION

PATENT NO. : 5,827,838            Page 2 of 3
DATED : October 27, 1998
INVENTOR(S) : LOUIS HARTOG COHEN ET AL.

It is certified that error appears in the above-identified patent and that said Letters Patent is hereby corrected as shown below:

In Column 10, claim 6, line 32, "claim 4" should read --claim 5--.

In Column 10, claim 7, line 38, "claim 5" should read --claim 6--.

In Column 10, claim 8, line 40, "claim 6" should read --claim 7--.

In Column 11, claim 9, line 24, "C30" should read --$C_{30}$--.

In Column 11, claim 10, line 34, "claim 8" should read --claim 9--.

In Column 12, claim 11, line 9, "claim 9" should read --claim 10--.

In Column 12, claim 12, line 15, "claim 10" should read --claim 11-.

in Column 12, claim 13, line 17, "claim 11" should read --claim 12--.

UNITED STATES PATENT AND TRADEMARK OFFICE
CERTIFICATE OF CORRECTION

PATENT NO. : 5,827,838
DATED : October 27, 1998
INVENTOR(S) : LOUIS HARTOG COHEN ET AL.

It is certified that error appears in the above-identified patent and that said Letters Patent is hereby corrected as shown below:

In Column 12, claim 13, line 17, "$X^1-X^2-A^2$" should read --$X^1-A^1-X^2-A^2$--.

In Column 12, claim 14, line 20, "claim 8" should read --claim 9--.

In Column 12, claim 15, line 22, "claim 8" should read --claim 9--.

In Column 12, claim 16, line 24, "claim 8" should read --claim 9--.

Signed and Sealed this

Eighteenth Day of May, 1999

Attest:

*Attesting Officer*

Q. TODD DICKINSON

*Acting Commissioner of Patents and Trademarks*